(12) United States Patent
Munson et al.

(10) Patent No.: US 8,202,899 B2
(45) Date of Patent: Jun. 19, 2012

(54) PYRAZOLE UREA DERIVATIVES USED AS KINASE INHIBITORS

(75) Inventors: Mark C. Munson, Louisville, CO (US); Brian C. Baer, Erie, CO (US)

(73) Assignee: Array BioPharma Inc., Boulder, CO (US)

( * ) Notice: Subject to any disclaimer, the term of this patent is extended or adjusted under 35 U.S.C. 154(b) by 209 days.

(21) Appl. No.: 12/668,005

(22) PCT Filed: Jul. 18, 2008

(86) PCT No.: PCT/US2008/070416
§ 371 (c)(1),
(2), (4) Date: Jan. 6, 2010

(87) PCT Pub. No.: WO2009/015000
PCT Pub. Date: Jan. 29, 2009

(65) Prior Publication Data
US 2010/0331385 A1    Dec. 30, 2010

Related U.S. Application Data

(60) Provisional application No. 60/951,832, filed on Jul. 25, 2007.

(51) Int. Cl.
*A61K 31/415* (2006.01)
*C07D 231/56* (2006.01)
(52) U.S. Cl. ..................... 514/407; 548/362.5
(58) Field of Classification Search .................. 514/407; 548/362.5
See application file for complete search history.

(56) References Cited

U.S. PATENT DOCUMENTS

| 7,521,447 | B2 | 4/2009 | Munson et al. |
| 7,799,782 | B2 * | 9/2010 | Munson et al. ............ 514/234.5 |
| 2009/0023795 | A1 | 1/2009 | Groneberg et al. |

OTHER PUBLICATIONS

International Search Report corresponding to related PCT Application No. PCT/US2008/070416, 2008.

* cited by examiner

*Primary Examiner* — Rei-tsang Shiao
(74) *Attorney, Agent, or Firm* — John R. Moore; Sarah S. Mastous

(57) ABSTRACT

Compounds of Formula (I) where $R^1$ and $R^2$ are as defined herein, and pharmaceutically acceptable salts thereof, are useful in the treatment and prevention of various disorders mediated by kinases.

6 Claims, No Drawings

PYRAZOLE UREA DERIVATIVES USED AS KINASE INHIBITORS

This invention relates to kinase inhibitors, pharmaceutical compositions containing the inhibitors, and methods for preparing these inhibitors. Certain embodiments of the present invention relate to metabolites of a particular indazole useful for inhibition of p38. The kinase inhibitors of this invention are useful for the treatment of inflammation, pain, osteoarthritis, rheumatoid arthritis, cancer, autoimmune diseases, and other cytokine-mediated diseases.

A number of chronic and acute inflammatory conditions have been associated with the overproduction of pro-inflammatory cytokines. Such cytokines include but are not limited to tumor necrosis factor alpha. (TNF-α), interleukin I beta (IL-1β), interleukin 8 (IL-8) and interleukin 6 (IL-6). Rheumatoid arthritis (RA) is a chronic disease where TNF-α and IL-1β are implicated in the onset of the diseases and in the progression of the bone and joint destruction seen with this debilitating condition. Recently approved therapeutic treatments for RA have included soluble TNF-α receptor (ENBREL™) and IL-1 receptor antagonist (ANAKINRA™). These treatments work by blocking the ability of their respective cytokines to bind to their natural receptors. Alternative methods for treating cytokine-mediated diseases are currently under investigation. One such method involves inhibition of the signaling pathway that regulates the synthesis and production of pro-inflammatory cytokines such as p38.

P38 (also known as CSBP or RK) is a serine/threonine mitogen-activated protein kinase (MAPK) that has been shown to regulate pro-inflammatory cytokines. P38 MAPK was first identified as a kinase that becomes tyrosine phosphorylated in mouse monocytes following treatment with lipopolysaccharide (LPS). A link between p38 MAPK and the response of cells to cytokines was first established by Saklatvala et al., (*Cell,* 1994, 78:1039-1049), who showed that IL-1 activates a protein kinase cascade that results in the phosphorylation of the small heat shock protein, Hsp27, probably by mitogen-activated protein activated protein kinase 2 (MAPKAP kinase-2). Analysis of peptide sequences derived from the purified kinase indicated that it was related to the p38 MAPK activated by LPS in mouse monocytes (Han, J., et al., *Science,* 1994, 265:808-811). At the same time it was shown that p38 MAPK was itself activated by an upstream kinase in response to a variety of cellular stresses, including exposure to UV radiation and osmotic shock, and the identity of the kinase that directly phosphorylates Hsp27 was confirmed as MAPKAP kinase-2 (Rouse, J., et al., *Cell,* 1994, 78:1027-1037). Subsequently, it was shown that p38 MAPK was the molecular target of a series of pyridinylimidazole compounds that inhibited the production of TNF from LPS-challenged human monocytes (Lee, J., et al., *Nature,* 372:739-746). This was a key discovery and has led to the development of a number of selective inhibitors of p38 MAPK and the elucidation of its role in cytokine signaling.

It is now known that multiple forms of p38 MAPK (α, β, γ, δ), each encoded by a separate gene, form part of a kinase cascade involved in the response of cells to a variety of stimuli, including osmotic stress, UV light, and cytokine mediated events. These four isoforms of p38 are thought to regulate different aspects of intracellular signaling. Activation of p38 is part of a cascade of signaling events that lead to the synthesis and production of pro-inflammatory cytokines such as TNF-α. P38 functions by phosphorylating downstream substrates that include other kinases and transcription factors. Agents that inhibit p38 MAPK, have been shown to block the production of cytokines including but not limited to TNF-α, IL-6, IL-8 and IL-1β in vitro and in vivo models (Adams, J. L., et al., *Progress in Medicinal Chemistry,* 2001, 38:1-60).

Abl (also known as Ableson) is a tyrosine kinase that is expressed in hematopoietic cells and is implicated in the progression of various liquid tumors including chronic myeloid leukemia (CML) and acute lymphoblastic leukemia (ALL). Transformation is a result of a chromosomal translocation, known as the Philadelphia chromosome. This leads to a constitutively activated chimera between Ableson and the breakpoint cluster region (BCR)—the Abl-BCR protein. GLEEVEC®, also known as Imatinib (Novartis) is a potent inhibitor of Abl and is currently used to treat CML patients (*N. Engl. J. Med.,* 2001, 344:1031-1037). This drug has become the standard of care for this deadly disease and is also being looked at in a variety of other cancer settings including gastrointestinal stromal tumors (GIST).

There is evidence that fibroblasts respond to the growth factor protein TGF-β by stimulating the Abl pathway and lead to morphological changes indicative of fibrosis; therefore Abl could play a role in the pathogenesis of fibrotic diseases like idiopathic pulmonary fibrosis. Leof et al. (*J. Clin. Invest,* 2004, 114(9) 1308-1316) have demonstrated pre-clinical efficacy of GLEEVEC® in a bleomycin-mediated model of lung fibrosis in mice. GLEEVEC® is being evaluated in patients with pulmonary fibrosis.

TEK (also known as Tie-2) is another receptor tyrosine kinase expressed only on endothelial cells which has been shown to play a role in angiogenesis. The binding of the factor angiopoietin-1 results in autophosphorylation of the kinase domain of TEK and results in a signal transduction process which appears to mediate the interaction of endothelial cells with peri-endothelial support cells, thereby facilitating the maturation of newly formed blood vessels. The factor angiopoietin-2, on the other hand, appears to antagonize the action of angiopoietin-1 on TEK and disrupts angiogenesis (Maisonpierre et al., *Science,* 1997, 277:55-60), Tie2 is upregulated in tumor angiogenic vessels (Trogan, E. Br. *J. Cancer,* 1998, 77:51-56) and there is evidence that it may play a supportive role in hematopoietic cancers (L. Naldini et al., *Cancer Cell,* 2005, 8:211-226; Such, T. et al, *Cell,* 2004, 118:149-161). In addition to its possible role in cancer, angiogenesis may also have implications in diseases like rheumatoid arthritis (RA), psoriasis and the progression of inflammation driven pathologies. The formation of pannus, the destructive legion responsible for arthritic progression is in part driven by new blood vessel formation and a recent paper by Lin, C. et al. (*Arthritis and Rheumatism,* 2005, 52(5): 1585-1594) demonstrates the pathological role of Tie2 in a mouse collagen-induced arthritis models of RA. Therefore, inhibition of Tie2 could provide a beneficial effect against proliferative and inflammatory diseases.

Peripheral blood monocytes (PBMCs) have been shown to express and secrete pro-inflammatory cytokines when stimulated with lipopolysaccharide (LPS) in vitro. P38 inhibitors efficiently block this effect when PBMCs are pretreated with such compounds prior to stimulation with LPS (Lee, J. C., et al., *Int. Immunopharmacol.,* 1988, 10:835-843). The efficacy of p38 inhibitors in animal models of inflammatory disease has prompted an investigation of the underlying mechanism(s), which could account for the effect of these inhibitors. The role of p38 in the response of cells to IL-1 and INF has been investigated in a number of cells systems relevant to the inflammatory response using a pyridinyl imidazole inhibitor: endothelial cells and IL-8 (Hashimoto, S., et al., *J. Pharmacol. Exp. Ther.,* 2001, 293:370-375), fibroblasts and IL-6/GM-CSF/PGE2 (Beyaert, R., et al., *EMBO J.,* 1996, 15:1914-1923), neutrophils and IL-8 (Albanyan, E. A., et al., *Infect. Immun.*, 2000, 68:2053-2060) macrophages and IL-1 (Caivano, M. and Cohen, P., *J. Immunol.*, 2000, 164:3018-3025), and smooth muscle cells and RANTES (Maruoka, S., et al., *Am. J. Respir. Crit. Care Med.*, 1999, 161:659-668). The destructive effects of many disease states are caused by the over production of pro-inflammatory cytokines. The ability of p38 inhibitors to regulate this overproduction makes them excellent candidates for disease modifying agents.

Known inhibitors of p38 MAPK are active in a variety of widely recognized disease models. Inhibitors of p38 MAPK show positive effects in a number of standard animal models of inflammation including rat collagen-induced arthritis (Jackson, J. R., et al., *J. Pharmacol. Exp. Ther.*, 1998, 284: 687-692); rat adjuvant-induced arthritis (Badger, A. M., et al., *Arthritis Rheum.*, 2000, 43:175-183; Badger, A. M., et al., *J. Pharmacol. Exp. Ther.*, (1996) 279:1453-1461); and carrageenan-induced paw edema in the mouse (Nishikori, T., et al., *Eur. J. Pharm.*, 2002, 451:327-333). Molecules that block the function of p38 have been shown to be effective in inhibiting bone resorption, inflammation, and other immune and inflammation-based pathologies in these animal models.

Thus, a safe and effective kinase inhibitor would provide a means to treat diseases and disorders that can be regulated by modulation of one or more kinases.

International patent application publication number WO 2004/078116 discloses certain indazole compounds as kinase inhibitors. Amongst these compounds are certain N1-substituted indazole derivatives having a substituent at the 5-position that contains a pyrazol-5-ylurea group. An example of such a compound includes the compound of Example 138 in which the N1 substituent is a 2-hydroxy-2-methylpropyl group.

There remains a need for compounds that are potent kinase inhibitors which preferably have improved aqueous solubility.

In Applicant's unpublished co-pending International patent application number PCT/US07/002272 filed on Jan. 26, 2007, which is incorporated herein by reference in its entirety, a number of indazole compounds useful for inhibiting p38 are disclosed. Among these compounds is the following, which is referred to herein as "Compound A":

Compound A

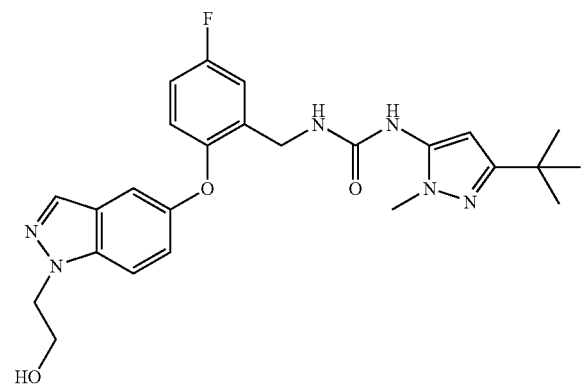

It has now been found that compounds having particularly desirable properties may also be obtained by selecting the primary alcohol group, —CH₂CH₂OH, as the N1 substituent, and a particular substituent at the 5-position containing a hydroxylated 3-tert-butyl-1-p-tolyl-1H-pyrazol-5-yl group.

In one aspect, the invention provides a compound having the Formula I:

I

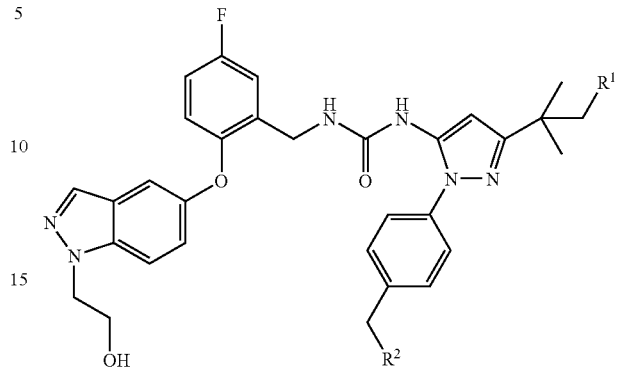

or a pharmaceutically acceptable salt thereof, wherein one of $R^1$ and $R^2$ is OH, the other being hydrogen.

In one embodiment of the compound of Formula I, $R^1$ is OH and $R^2$ is H. Such compound can be represented by the Formula Ia:

Ia

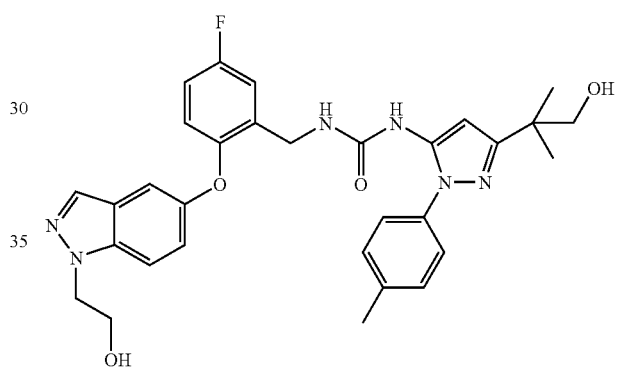

The compound of Formula :Ea may also be described by the chemical name 1-((5-fluoro-2-(1-(2-hydroxyethyl)-1H-indazol-5-yloxy)phenyl)methyl)-3-(3-(1-hydroxy-2-methylpropan-2-yl)-1-p-tolyl-1H-pyrazol-5-yl)urea. The synthesis of compound Ia is described in Example 1.

In another embodiment of the compound of Formula I, $R^1$ is H and $R^2$ is OH. Such compound can be represented by the Formula Ib Ib

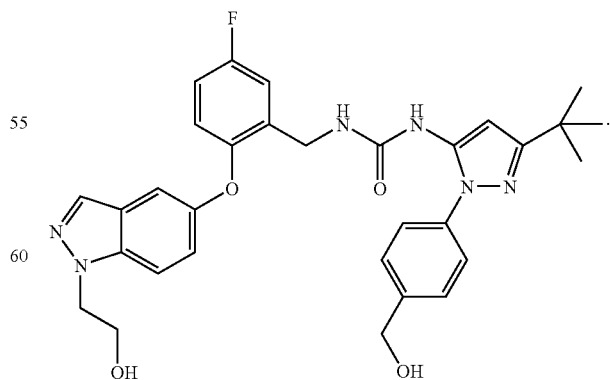

The compound of Formula Ib may also be described by the chemical name 1-(3-tert-butyl-1-(4-(hydroxymethyl)phenyl)-1H-pyrazol-5-yl)-3-(5-fluoro-2-(1-(2-hydroxyethyl)-1H-indazol-5-yloxy)benzyl)urea. The synthesis of compound Ib is described in Example 2.

Compounds Ia and Ib were initially identified as metabolites of Compound. A disclosed in Applicant's unpublished co-pending international patent application number PCT/US07/002272 filed on Jan. 26, 2007.

It was found the compound of Formula Ia has improved selectivity against certain kinases. It was further found the compound of Formula Ia has improved aqueous solubility. In addition, the compound of Formula Ia possesses at least one unique position for creating soltible prodrugs.

More particularly, it was discovered that the compound of Formula Ia has improved aqueous solubility compared to the compound of Example 138 of WO 2004/078116 at pH 6.5 and 7.4. Furthermore, unlike compound Ia, the compound of Example 138 of WO 2004/078116 does not possess at least one primary alcohol group that can be derivatized to afford a prodrug.

It was also found the compound of Formula Ib has improved potency against certain kinases. In addition, the compound of Formula Ib possess at least one unique position for creating soluble prodrugs.

More particularly, as demonstrated with test data hereinafter, the compound of Formula Ib has been found to be a significantly more potent inhibitor of p38 than the compound of Example 138 of WO 2004/078116. Furthermore, unlike compound Ib, the compound of Example 138 of WO 2004/078116 does not possess a primary alcohol group that can be derivatized to afford a prodrug.

In a further embodiment, the invention is directed to a pure and isolated form of the compound of Formula I or a pharmaceutically acceptable salt thereof. In one embodiment, the invention provides a pure and isolated form of the compound of Formula Ia or a pharmaceutically acceptable salt thereof. In another embodiment, the invention provides a pure and isolated form of the compound of Formula Ib or a pharmaceutically acceptable salt thereof.

The term "isolated" or "isolated form" for a compound of Formula I refers to the physical state of said compound after being isolated from a synthetic process or natural source or combination thereof. The term "pure" or "pure form" for a compound of Formula I refers to the physical state of said compound after being obtained from a purification process or processes described herein or well known to one skilled in the art, in sufficient purity to be characterizable by standard analytical techniques described herein or well know to one skilled in the art.

Accordingly, a further aspect of the invention provides a compound of Formula I or a pharmaceutically acceptable salt thereof when prepared by a synthetic process or an ex vivo process.

In addition to compound of Formulas I, the invention also includes pharmaceutically acceptable salts of these compounds. The compounds of Formulas I also include other salts of such compounds which are not necessarily pharmaceutically acceptable salts, and which may be useful as intermediates for preparing and/or purifying compounds of Formulas I and/or for separating enantiomers of compounds of Formulas I.

It will further be appreciated that the compounds of Formulas I or their salts may be isolated in the form of solvates, and accordingly that any such solvate is included within the scope of the present invention.

The phrase "pharmaceutically acceptable" indicates that the compound or composition is compatible chemically and/or toxicologically with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

Also provided herein are prodrugs of the compound of Formula I.

A "prodrug" is a compound that may be converted under physiological conditions or by solvolysis to the specified compound or to a salt of such compound.

Any of the free hydroxy group of the compound of this invention may be derivatized as a prodrug by converting a hydroxy group, for example the hydroxyethyl group on the indazole N1 position, into a group such as, but not limited to, a phosphate ester, hemisuccinate, dimethylaminoacetate, or phosphoryloxymethyloxycarbonyl group, as outlined in *Advanced Drug Delivery Reviews*, 1996, 19, 115. Carbamate prodrugs of hydroxy groups are also included, as are carbonate prodrugs, sultanate esters and sulfate esters of hydroxy groups. Derivatization of hydroxy groups as (acyloxy)methyl and (acyloxy)ethyl ethers, wherein the acyl group may be an alkyl ester optionally substituted with groups including, but not limited to, ether, amine and carboxylic acid functionalities, or where the acyl group is an amino acid ester as described above, are also encompassed. Prodrugs of this type are described in *J. Med Chem.*, 1996, 39, 10. More specific examples include replacement of the hydrogen atom of the alcohol group with a group such as $(C_1-C_6)$alkanoyloxymethyl, 1-$((C_1-C_6)$alkanoyloxy)ethyl, 1-methyl-1-$((C_1-C_6)$alkanoyloxy)ethyl, $(C_1-C_6)$alkoxycarbonyloxymethyl, N-$(C_1-C_6)$alkoxycarbonylaminomethyl, succinoyl, $(C_1-C_6)$ alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$ alkyl$)_2$ or glycosyl (the radical resulting from the removal of a hydroxyl group of the hemiacetal form of a carbohydrate). Without wishing to be bound by theory, it is believed that a phosphate ester derivative of a compound of Formula I will function as a pro-drug for the corresponding (primary alcohol.

It will be appreciated that certain compounds according to the invention may contain one or more centers of asymmetry and may therefore be prepared and isolated in a mixture of isomers such as a racemic mixture, or in an enantiomerically pure form.

The compounds of this invention may be prepared by synthetic routes that include processes analogous to those well known in the chemical arts, or as described in international patent application, publication number WO 2004/078116, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Auft, ed. Springer-Verlag, Berlin, including supplements (also available via the Beilstein online database).

According to another aspect, the present invention provides a process for the preparation of a compound of Formula I or a pharmaceutically acceptable salt thereof, which comprises:

(a) coupling a compound of formula III

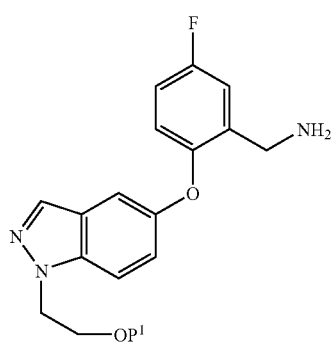

or a salt thereof, in which $P^1$ represents a hydrogen atom or a hydroxyl protecting group, with a compound of formula IV

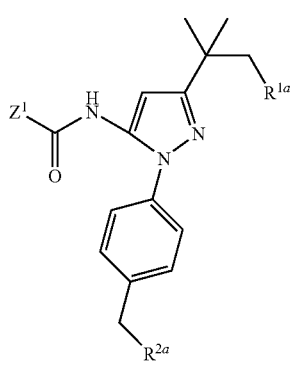

in which $Z^1$ represents a leaving group, or the corresponding isocyanate, and one of $R^{1a}$ and $R^{2a}$ is H and the other is $OP^2$ wherein $P^2$ is as defined for $P^1$; or (b) for a compound of Formula I wherein $R^1$ is H and $R^2$ is OH, treating a corresponding compound of formula V

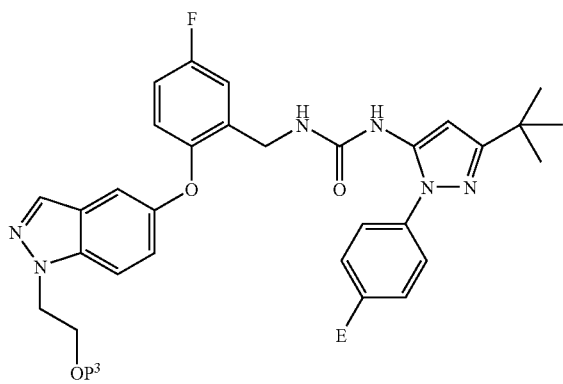

where $P^3$ is as defined for $P^1$ and E is CN, $CO_2$(1-3C alkyl), or C(=O)H, with one or more reducing agents capable of reducing the E group to a hydroxymethyl group;

followed by removing any protecting group and, if desired, forming a pharmaceutically acceptable salt.

Examples of convenient hydroxyl protecting groups represented by $P^1$ and $P^2$ include tri(1-4C alkyl)silyl groups such as trimethylsilyl (TMS) and t-butyldimethylsilyl (TBDMS), aralkyl groups such as benzyl, acyloxy groups such as (1-6C) alkanoyloxy groups, and cyclic hemiketals, such as tetrahydro-2H-pyran-2-yl.

The leaving group represented by $Z^1$ may be, for example an unsubstituted or substituted hydrocarbyloxy group, for example a halo(1-6C)alkoxy group, such as 2,2,2-trichloroethoxy, an alkenyloxy group such as $CH_2=C(CH_3)O-$, or an aryloxy group optionally substituted, for example, with one or more groups selected from F, Cl, Br, and $NO_2$. Particular values for an optionally substituted aryloxy group include phenoxy, 4-chlorophenoxy, 4-bromophenoxy, 4-fluorophenoxy, 4-nitrophenoxy, and 2-nitrophenoxy. In certain embodiments, Z is 2,2,2-trichloroethoxy.

The coupling of a compound of formula (III) with a compound of formula (IV) when $Z^1$ is a halo(1-6C)alkoxy group, such as 2,2,2-trichloroethoxy, or an optionally substituted phenoxy group can be conveniently performed at a temperature between 0 and 100° C., and more particularly at ambient temperature. Convenient solvents include aprotic solvents such as ethers (for example tetrahydrofuran or p-dioxane), DMF, DMSO, or acetonitrile. Alternatively, the reaction can be performed neat (i.e., in the absence of an additional solvent). The coupling reaction is conveniently performed in the presence of a base such as a tertiary amine (for example, triethylamine or DMA).

Referring to method (b), when the E group is CN, the nitrile group can be reduced to a hydroxymethyl group, for example, in a stepwise manner. More particularly, the nitrile can first be reduced to an aldehyde using a suitably mild reducing agent, for example diisobutylaluminum hydride (DIBAL) in a suitable solvent such as dichloromethane, followed by reduction of the aldehyde to a hydroxymethyl group using a suitably mild reducing agent such as sodium borohydride in a suitable solvent such as methanol. The reactions can be conveniently performed at a temperature between 0 and 100° C., and more particularly at ambient temperature. When the E group is $CO_2$(1-3C alkyl), for example $CO_2Et$, the ester group can be reduced to a hydroxymethyl group using a suitably mild reducing agent such as sodium borohydride in a suitable solvent such as methanol.

A compound of Formula (V) can be prepared by coupling a corresponding compound of Formula (III)

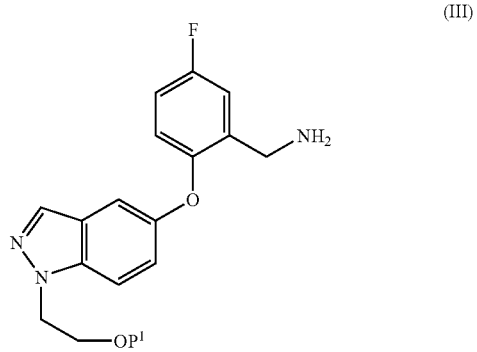

or a salt thereof, with a compound of Formula (VI)

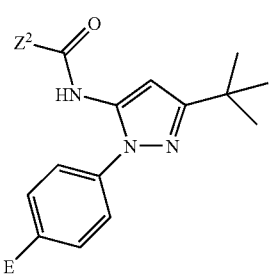

(VI)

in which $Z^2$ is as defined for $Z^1$.

The compounds of the formulas (III), (IV), (V) and (VI) are believed to be novel and are provided as a further aspects of the invention.

The compounds of the invention may be used to treat diseases mediated by modulation or regulation of protein kinases. Accordingly, another aspect of the present invention provides a method of treating or preventing a kinase-mediated condition, comprising administering a compound of Formula I to a mammal in need thereof in an amount effective to treat or prevent said kinase-mediated condition. In one embodiment, the compound of Formula I is in a pure and isolated form.

An "effective amount" refers to an amount of compound that, when administered to a mammal in need of such treatment, is sufficient to effect treatment for a disease mediated by the activity of one or more protein kinases, such as p38 MAPK, and the associated kinase-mediated events such as cytokine production. Thus, for example, a therapeutically effective amount of a compound of this invention or a salt thereof, is a quantity sufficient to modulate, regulate, or inhibit the activity of one or more protein kinases such that a disease condition which is mediated by that activity is reduced or alleviated.

"Treating" is intended to mean at least the mitigation of a disease condition in a mammal, such as a human, that is affected, at least in part, by the activity of one or more protein kinases. The terms "treat" and "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition Or disorder or those in which the condition or disorder is to be prevented.

The amount of a compound of this invention administered to a mammal will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

In one aspect of this invention, the compounds of this invention or pharmaceutical salts thereof may be formulated into pharmaceutical compositions for administration to a mammal to treat or prevent a kinase-mediated condition. The term "kinase-mediated condition" as used herein means any disease or other deleterious condition in which p38 is known to play a role, and includes conditions that are known to be caused by IL-1, TNF, IL-6 or IL-8 overproduction. Such conditions include, but are not limited to, inflammatory diseases, autoimmune diseases, destructive bone disorders, proliferative disorders, infectious diseases, viral disease, fibrotic disease and neurodegenerative diseases.

Inflammatory diseases which may be treated or prevented include, but are not limited to, acute pancreatitis, chronic pancreatitis, asthma, allergies, and adult respiratory distress syndrome.

Autoimmune diseases which may be treated or prevented include, but are not limited to, glomerulonephritis, rheumatoid arthritis, systemic lupus erythematosus, scleroderma, chronic thyroiditis. Graves disease, autoimmune gastritis, insulin-dependent diabetes mellitus (Type I), autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, and graft vs. host disease.

Destructive bone disorders which may be treated or prevented include, but are not limited to, osteoporosis, osteoarthritis and multiple myeloma-related bone disorder.

Fibrotic diseases which may be treated or prevented include, but are not limited to, idiopathic pulmonary fibrosis, kidney and liver fibrosis.

Proliferative diseases which may be treated or prevented include, but are not limited to, acute myelogenous leukemia, chronic myelogenous leukemia, metastatic melanoma, Kaposi's sarcoma, myelodysplastic syndrome, multiple myeloma, astrocytoma, bone cancer, brain cancer, breast cancer, colorectal cancer, gastric cancer, glioma, glioblastoma, multiforme, head and neck cancer, hematological cancer, hematopoiesis disorders, interstitial lung diseases, Kaposi's sarcoma, lymphocytic leukemia, melanoma, myeloid leukemia, non-small cell lung cancer, ovarian cancer, prostate cancer, sarcoma, skin cancer, small cell lung cancer, and stomach cancer. Other patients which can be treated include those undergoing bone marrow transplantation.

Infectious diseases which may be treated or prevented include, but are not limited to, sepsis, septic shock, and Shigellosis.

Viral diseases which may be treated or prevented include, but are not limited to, acute hepatitis infection (including hepatitis A, hepatitis B and hepatitis C), HIV infection and CMV retinitis.

Degenerative conditions or diseases which may be treated or prevented by the compounds of this invention include, but are not limited to, Alzheimer's disease, Parkinson's disease, cerebral ischemia and other neurodegenerative diseases.

The term "kinase-mediated conditions" also includes ischemia/reperfusion in stroke, heart attacks, myocardial ischemia, organ hypoxia, vascular hyperplasia, cardiac hypertrophy and thrombin-induced platelet aggregation.

In addition, the kinase inhibitors of this invention arc also useful for inhibiting the expression of inducible pro-inflammatory proteins such as prostaglandin endoperoxide synthase-2 (PGHS-2), also referred to as cyclooxygenase-2

(COX-2). Therefore, other "kinase-mediated conditions" include, but are not limited to, edema, analgesia, fever and pain, such as neuromuscular pain, headache, cancer pain, dental pain and arthritis pain.

The conditions and diseases that may be treated or prevented by the kinase inhibitors of this invention may also be conveniently grouped by the cytokine (e.g., IL-1, TNF, IL-6, IL-8) that is believed to be responsible for the disease.

Thus, an IL-1-mediated disease or condition includes rheumatoid arthritis, osteoarthritis, stroke, endotoxemia and/or toxic shock syndrome, inflammatory reaction induced by endotoxin, inflammatory bowel disease, tuberculosis, atherosclerosis, muscle degeneration, cachexia, psoriatic arthritis, Reiter's syndrome, gout, traumatic arthritis, rubella arthritis, acute synovitis, diabetes, pancreatic β-cell disease and Alzheimer's disease.

TNF-mediated diseases or conditions include, but are not limited to, rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, cachexia secondary to infection, AIDS, ARC or malignancy, keloid formation, scar tissue formation, Crohn's disease, ulcerative colitis or pyresis. TNF-mediated diseases also include viral infections, such as HIV, CMV, influenza and herpes; and veterinary viral infections, such as lentivirus infections, including, but not limited to equine infectious anemia virus, caprine arthritis virus, visna virus or maedi virus; or retrovirus infections, including feline immunodeficiency virus, bovine immunodeficiency virus, or canine immunodeficiency virus.

IL-8 mediated diseases or conditions include, but are not limited to, diseases characterized by massive neutrophil infiltration, such as psoriasis, inflammatory bowel disease, asthma, cardiac and renal reperfusion injury, adult respiratory distress syndrome, thrombosis and glomerulonephritis.

In addition, the compounds of this infection may be used topically to treat or prevent conditions caused or exacerbated by IL-1 or TNF. Such conditions include, but are not limited to, inflamed joints, eczema, psoriasis, inflammatory skin conditions such as sunburn, inflammatory eye conditions such as conjunctivitis, pyresis, pain and other conditions associated with inflammation.

Although the compounds of this invention are primarily of value as therapeutic agents for use in warm-blooded animals (including humans), they are also useful whenever it is required to inhibit the effects of cytokines. Thus, they are useful as pharmacological standards for use in the development of new biological tests and in the search for new pharmacological agents.

The size of the dose for therapeutic or prophylactic purposes of a cornpound of this invention will naturally vary according to the nature and severity of the conditions, the age and sex of the animal or patient and the route of administration, according to well known principles of medicine.

The compounds of this invention may be used in combination with other drugs and therapies used in the treatment of disease states which would benefit from the inhibition of kinases and the associated cytokines, such as IL-1, TNF, IL-6 or IL-8. The dose of the second drug can be appropriately selected based on a clinically employed dose. The proportion of the compound of this invention and the second drug can be appropriately determined according to the administration subject, the administration route, the target disease, the clinical condition, the combination, and other factors. In cases where the administration subject is a human, for instance, the second drug may be used in an amount of 0.01 to 100 parts by weight per part by weight of the compound of this invention.

The second drug of the pharmaceutical combination formulation or dosing regimen has, for example, complementary activities to the compound of this invention such that they do not adversely affect each other. Such drugs are suitably present in combination in amounts that are effective for the purpose intended. Accordingly, another aspect of this invention provides a composition comprising a compound of this invention in combination with a second drug, such as described herein.

The compound of this invention and the additional pharmaceutically active drug(s) may be administered together in a unitary pharmaceutical composition or separately and, when administered separately this may occur simultaneously or sequentially in any order. Such sequential administration may be close in time or remote in time. The amounts of the compound of this invention and the second drug(s) and the relative timings of administration will be selected in order to achieve the desired combined therapeutic effect.

The combination therapy may provide "synergy" and prove "synergistic", i.e., the effect achieved when the active ingredients used together is greater than the sum of the effects that results from using the compounds separately. A synergistic effect may be attained when a compound of this invention and the second drug are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when a compound of this invention and the second drug are administered or delivered sequentially, e.g., by different injections in separate syringes. For example, during alternation therapy, an effective dosage of each active ingredient can be administered sequentially, i.e., serially, whereas in combination therapy, effective dosages of two or more active ingredients are administered together.

For example, by virtue of their ability to inhibit cytokines, the compounds of this invention are of value in the treatment of certain inflammatory and non-inflammatory diseases which are currently treated with a cyclooxygenase-inhibitory non-steroidal anti-inflammatory drug (NSAID) such as indomethacin :ketorolac, acetylsalicylic acid, ibuprofen, sulindac, tolmetin and piroxicam. Co-administration of a compound of this invention with a NSAID can result in a reduction of the quantity of the tatter agent needed to produce a therapeutic effect, and thus the likelihood of adverse side-effects from the NSAID such as gastrointestinal effects are reduced. Thus according to a further feature of the invention there is provided a pharmaceutical composition which comprises a compound of this invention, or a pharmaceutically-acceptable salt thereof in conjunction or admixture with a cyclooxygenase inhibitory non-steroidal anti-inflammatory agent, and a pharmaceutically-acceptable diluent or carrier.

The compounds of this invention may also be used in the treatment of conditions such as rheumatoid arthritis in combination with anti-arthritic agents such as gold, methotrexate, steroids and penicillinamine, and in conditions such as osteoarthritis combination with steroids.

The compounds of this invention may also be used in the treatment degradative diseases, for example osteoarthritis in combination with chondroprotective, anti-degradative and/or reparative agents such as Diacerhein, hyaturonic acid formulations such as Hyalgata, Rumaion, and Arteparon, and glucosamine salts such as Antril.

The compounds of this invention may also be used in the treatment of asthma in combination with anti-asthmatic agents such as bronchodilators and leukotriene antagonists.

The compounds of the invention may be administered by any route appropriate to the condition to be treated. Suitable routes include oral, parenteral (including subcutaneous, intramuscular, intravenous, intraarterial, intradennal, intrathecal and epidural), transdermal, rectal, nasal, topical (including buccal and sublingual), vaginal, intraperitoneal, intrapulmonary and intranasal. It will be appreciated that the route used may vary with, for example, the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

Thus, a further aspect of this invention includes a pharmaceutical composition comprising a compound of Formula I or a pharmaceutically acceptable salt thereof and a pharmaceutically acceptable carrier. In one embodiment, the compound of Formula I is compound Ia. In another embodiment, the compound of Formula I is compound Ib. In one embodiment, the compound of Formula I or a pharmaceutically acceptable salt thereof is in a pure and isolated form.

The pharmaceutical compositions of this invention may be prepared for various routes and types of administration. For example, a compound of this invention having the desired degree of purity may optionally be mixed with pharmaceutically acceptable carriers. The pharmaceutical formulations may further include diluents, excipients and/or stabilizers (Remington's Pharmaceutical Sciences (1980) 16th edition, Osol, A. Ed.), in the form of a lyophilized formulation, a milled powder, or an aqueous solution.

The particular carrier, diluent or excipient used will depend upon the means and purpose for which the compound of this invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water.

Sustained-release preparations of compounds of this invention may be prepared. Suitable examples of sustained-release preparations include semipermeable matrices of solid hydrophobic polymers containing a compound of this invention, which matrices are in the form of shaped articles, e.g., films, or microcapsules. Examples of sustained-release matrices include polyesters, hydrogels (for example, poly(2-hydroxyethyl-methacrylate), or poly(vinytaicohop), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The pharmaceutical compositions of this invention may be in the form of a sterile injectable preparation, such as a sterile injectable aqueous or oleaginous suspension. This suspension may be formulated according to the known art using suitable dispersing or wetting agents and suspending agents. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employe(are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Pharmaceutical compositions of this invention suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The compositions of the invention may also be formulated in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder), or for transdermal administration (for example as transdermal skin patches).

The amount of a compound of this invention that is combined with one or more excipients to produce a single dosage form will necessarily vary depending upon the subject treated, the severity of the disorder or condition, the rate of administration, the disposition of the compound and the discretion of the prescribing physician. In one embodiment, a suitable amount of a compound of this invention is administered to a mammal in need thereof. Administration in one embodiment occurs in an amount between about 0.001 mg/kg of body weight to about 60 mg/kg of body weight per day. In another embodiment, administration occurs in an amount between 0.5 mg/kg of body weight to about 40 mg/kg of body weight per day. In some instances, dosage levels below the lower limit of the aforesaid range may be more than adequate, while in other cases still larger doses may be employed without causing any harmful side effect., provided that such larger doses are first divided into several small doses for administration throughout the day. For further information on routes of administration and dosage regimes, see Chapter 25.3 in Volume 5 of *Comprehensive Medicinal Chemistry* (Corwin Flansch; Chairman of Editorial Board), Pergamon Press 1990, which is specifically incorporated herein by reference.

According to another aspect, the present i vention provides the use of a compound of Formula I or a pharmaceutically acceptable salt thereof in the manufacture of a medicament for the treatment of a kinase-mediated condition in a mammal, In one embodiment, the compound of Formula I or a pharmaceutically acceptable salt thereof is in a pure and isolated form.

According to another aspect, the present invention provides a compound of Formula I or a pharmaceutically acceptable salt thereof, for use in therapy, such as the treatment of a kinase-mediated condition in a mammal. In one embodiment, the compound of Formula I or a pharmaceutically acceptable salt thereof is in a pure and isolated form.

The activity of the compounds of this invention may be assayed for p38 MAPK inhibition in vitro, in vivo, or in a cell line. In vitro assays include assays that determine inhibition of either the kinase activity or ATPase activity of activated p38 Alternative in vitro assays quantitate the ability of the inhibitor to bind to p38 MAPK and may be measured either by radiolabelling the inhibitor prior to binding, isolating the inhibitor/p38 MAPK complex and determining the amount of radiolabel bound, or by running a competition experiment where new inhibitors are incubated with p38 MAPK bound to known radioligands. These and other useful in vitro and cell culture assays are well known to those of skill in the art.

Cell culture assays of the inhibitory effect of the compounds of this invention may be used to determine the amounts of TNF-α, IL-1, IL-6 or IL-8 produced in whole blood or cell fractions thereof in cells treated with inhibitor as compared to cells treated with negative controls. Level of these cytokines may be determined through the use of commercially available ELISAs or as described in the Biological Examples section below.

EXAMPLES

In order to illustrate the invention, the following examples are included. However, it is to be understood that these examples do not limit the invention and are only meant to suggest a method of practicing the invention.

Biological Examples

Example A p38 Biochemical Assay p38 activity was assayed at room temperature in a 100 µL reaction containing 5 nM activated p38α enzyme and 1 µM ATF-2 (Activating Transcription Factor 2 fusion protein) as the substrate in 25 mN HEPES (pH 7.4), 100 µM Vanadate, 1 mM :DTT, 10 mM $MgCl_2$ and 10 µM [γ-$^{33}$P]-ATP (~0.1 µCi $P^{33}$/reaction). The reaction was terminated after 30-40 minutes by adding 25% TCA, allowed to stand for 5 minutes, and then transferred directly to a GF-B membrane filter plate. The filter was washed twice for 30 seconds with 0.5% phosphoric acid using a Tomtec Mach III Automated Harvestor. After washing, the vacuum was continued for 30 seconds to dry the filter. Approximately 30 µL of scintillant was added per well to the filter plate and then read in a Liquid Scintillation Counter (Packard TopCount HTS).

In this assay, the compounds of Examples 1 and 2 generated an $IC_{50}$ of <1.0 nM.

Example B

Human Whole Blood TNF-α Assay

In a functional cell assay, the compound of Examples 1 and 2 were tested for their ability to inhibit TNF-α production in whole blood treated with bacterial lipopolysaccharide (LPS) to induce cytokine production (as detected by ELISA).

Compound test solutions were made by making 3.33 fold serial dilutions in DMSO, which dilutions were then diluted to 5× stocks by diluting with MEM, 2% heat inactivated fetal bovine serum ("MS"), 20 mM HEPES, 2 mM L-glutamine, and 1% penicillin/streptomycin Whole blood was collected from human volunteers using sodium heparin Vacutainer™ tubes and processed within two hours of collection. Blood was diluted 3-fold with Whole Blood (WB) medium (RPMI 1640, 2% heat inactivated fetal bovine serum, 20 mM HEPES, 2 mM L-glutamine, and 1% penicillin/streptomycin). 100 µL of diluted blood was added to each well of a 96-well cell culture plate, followed by 30 µL of a compound test solution.

After a one-hour incubation at 37° C./5% $CO_2$, 20 µL of 7.5 ng/mL lipopolysaccharide (E. coli K-235, Sigma L2018) was added to each well. The cells were incubated again at 37° C./5% $CO_2$ for 16-20 hours. The test compound supernatants were collected and assayed for TNF-α content by ELISA methods.

Briefly, test compound supernatants were added to wells of a 96-well plate that were coated with antibody to human TNF-α (R&D Systems, MAB210) and incubated at room temperature for at least one hour. After washing with wash buffer, wells were incubated at room temperature with 100 µL of 0.2 µg/mL biotinylated goat anti-human TNF-α (R&D Systems, BAF210) in "antibody diluent" (20 mM HEPES, pH 7.4, 150 nM NaCl, 2 mM $MgCl_2$, 1% BSA, 0.02% Tween-20) for another hour. After washing, the plate was incubated with 100 µL of 0.02 µg/mL streptavidin-alkaline phosphatase in antibody diluent for an additional hour. 200 µL of the colorimetric substrate p-nitrophenyl phosphate (pNPP, 1 mg/mL) in diethanolamine buffer with a0.5 mM $MgCl_2$ was added to each well. After incubation at room temperature for 30-40 minutes, the reaction was stopped by the addition of 2N NaOH. The absorbance at 405 nm was then read.

In this assay, the compound of Example 1 generated an apparent $IC_{50}$ of 447 nM, and the compound of Example 2 generated an apparent $IC_{50}$ of 1.9 nM Example C Solubility Assay The solubility of each of the compounds of Examples 1 and 2 were tested at pHs 1.2, 6.5 and 7.4 using a modified shake flask method. The compounds were received as 1.6 mg/mL stock solutions in DMSO. Aqueous unknowns were prepared at final concentrations of 16 µg/mL and 32 µg/mL, with each aqueous unknown containing 1% or 2% DMSO, respectively. The aqueous samples were quantitated against organic standards prepared in MeOH (with 1% DMSO in the high standard (16 µg/mL). UV 220 nm and UV 254 nm area were used for quantitation.

TABLE 1

| | | Solubility (µg/mL) | | |
| --- | --- | --- | --- | --- |
| | Starting Conc. | pH 1.2 | pH 6.5 | pH 7.4 |
| Example 1 | 16 µg/mL (with 1% DMSO) | 7.9 | 0.75 | 0.7 |
| | 32 µg/mL (with 2% DMSO) | 18.8 | 1.8 | 1.7 |

By way of comparison, the solubility of the compound of Example 138 of WO 2004/078116 was also tested. The results are shown in Table 1a.

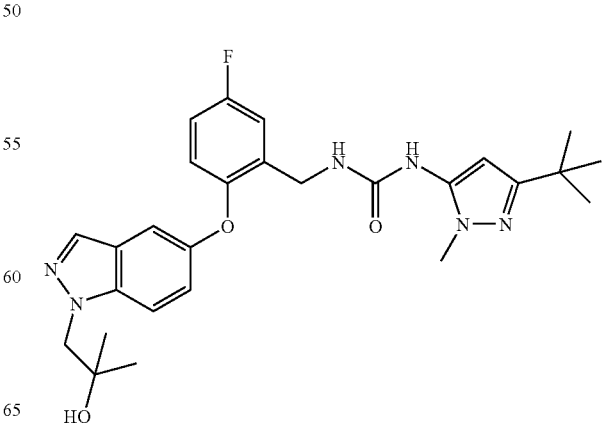

Example 138

TABLE 1a

|  | Starting Conc. (μg/mL) | Solubility (μg/mL) pH 7.4 |
|---|---|---|
| Example 138 | 1000 | 0.045 |

Preparative Examples

In the examples described below, unless otherwise indicated, all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), N,N-dimethytformamide (DMF), dichloromethane (DCM), toluene, dioxane and 1,2-difluoroethane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters).

$^1$H-NMR spectra were recorded on a Varian instrument operating at 400 MHz. $^1$H-NMR spectra were obtained as CDCl$_3$ or CD$_3$OD solutions (reported in ppm), using chloroform as the reference standard (7.25 ppm). Other NMR solvents were used as needed. When peak multiplicities are reported, the following abbreviations are used: s (singlet), d (doublet), t (triplet), m (multiplet), hr (broadened), dd (doublet of doublets), dt (doublet of triplets). Coupling constants, when given, are reported in Hertz (Hz).

Example 1

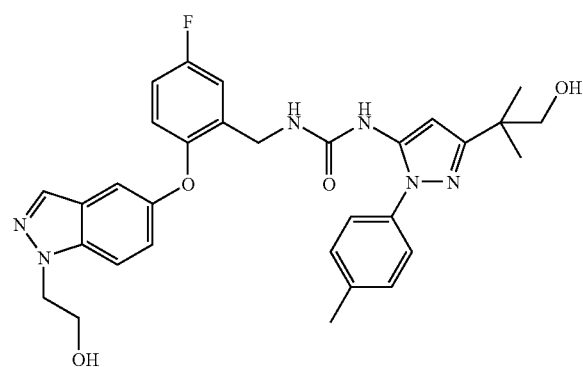

1-((5-Fluoro-2-(1-(2-hydroxyethyl)-1H-indazol-5-yloxy)phenyl)methyl)-3-(3-(1-hydroxy-2-methylpropan-2-yl)-2-p-tolyl-1H-pyrazol-5-yl)urea Step A: Preparation of methyl 3-(tert-butyldimethylsilyloxy)-2,2-dimethylpropanoate: Methyl 3-hydroxy-2,2-dimethylpropanoate (2.635 g, 19.94 mmol) tert-butylchlorodimethylsilane (2.855 g, 18.94 mmol), and 1H-imidazole (1.629 g, 23.93 mmol) were combined in DMF (15 and stirred overnight at ambient temperature. The reaction mixture was concentrated, and water and ethyl acetate were added to the residue. The crude product was extracted into the organic layer. The organic layer was washed with brine, dried over MgSO$_4$ and filtered, and the filtrate was concentrated and dried to provide 1.7 g of the title product. Very weak MS M+1 (246).

Step B: Preparation of 5-hydroxy-4,4-dimethyl-3-oxopentanenitrile: Methyl 3-(tert-butyldimethylsilyloxy)-2,2-dimethylpropanoate (0.63 g, 2.557 mmol) was added to toluene and NaH (0.4090 g, 10.23 mmol) and acetonitrile (0.534 mL, 10.23 mmol) and stirred overnight in a sealed vessel for 6 hours at 90° C. The solids were removed by filtration and rinsed with toluene. The toluene filtrate was concentrated, and the resulting solids were added to 3 N HCl, stirred for 30 minutes and then washed with ether. The mixture was concentrated and the resulting solids were rinsed several times with DCM. The DCM was dried over MgSO$_4$, filtered and evaporated to provide the title compound as an oil (320 mg), which was used directly in the next step.

Step C: Preparation of 2-(5-amino-1-p-tolyl-1H-pyrazol-3-yl)-2-methylpropan-1-ol: 5-hydroxy-4,4-dimethyl-3-oxopentanenitrile (0.32 g, 2.27 mmol) and 1-chloro-2-phenylhydrazine (0.361 g, 2.49 mmol) were combined in ethanol and heated at 90° C. for 8 hours. The reaction was cooled and concentrated, and the residue was triturated with ethyl acetate. The solids were collected by filtration, triturated with acetone and rinsed to isolate 36 mg of the title compound as a pure white solid. MS M+1(246).

Step D: Preparation of 2,2,2-trichloroethyl 3-(1-hydroxy-2-methylpropan-2-yl)-1-p-tolyl-1H-pyrazol-5-ylcarbamate: 2-(5-Amino-1-p-tolyl-1H-pyrazol-3-yl)-2-methylpropan-1-ol (0.0065 g, 0.0265 mmol) was combined with chloroformate (0.00504 mL, 0.0371 mmol) and 2 N NaOH (53 μL, 0.106 mmol) in ethyl acetate. Water (500 μL) was added, and the reaction mixture was stirred for 3-4 hours. The reaction mixture was diluted with water and ethyl acetate and the crude product was extracted into the organic layer. The organic layer was dried over MgSO$_4$, filtered and concentrated to provide the title product (10 mg), which was taken directly on to next step. MS M+1 (421).

Steps E1-E6: Preparation of 2-(5-(2-(aminomethyl)-4-fluorophenoxy)-1H-indazol-1-yl)ethanol dihydrochloride Step E1: Preparation of 2-(4-amino-3-methylphenoxy)-5-fluorobenzonitrile: In a 5 L flask that had been evacuated and back-filled with Argon, 2,5-difluorobenzonitrile (1092 mL, 3057 mmol) and 4-amino-3-methylphenol (376.5 g, 3057 mmol) were dissolved in dry DMSO (2.75 M) with rapid stirring at ambient temperature. The solution was evacuated/backfilled with Argon. Potassium carbonate (697.2 g, 5044 mmol) was added. The reaction was evacuated/backfilled with Argon and warmed to 81° C. for 14 hours. After cooling to ambient temperature, the reaction was poured slowly into 3 separate beakers, each containing 2.5 L of rapidly stirring ice water to prevent clumping. The residue in the round bottom flask was taken up in water repeatedly and poured into the beakers until a total volume of 3.5 L was realized in each of the three beakers. The suspension was stirred rapidly for 2 hours as it came to ambient temperature. The brown solids were collected by filtration, washed with water (15 L), air dried, dried with latex dam, and dried under high vacuum at 45° C. for 72 hours to provide 734 g (99%) of desired product as a tan solid. MS M+1 (243).

Step E2: Preparation of 2-(1-acetyl-1H-indazol-5-yloxy)-5-fluorobenzonitrile: In a 2 L flask, 2-(4-amino-3-methylphenoxy)-5-fluorobenzonitrile (277.1 ml, 221.7 mmol) was taken up in toluene (0.8 M) and treated with potassium acetate (26.11 g, 266.0 mmol) at ambient temperature. The reaction mixture was cooled to 0° C. and acetic anhydride (63.91 mL, 676.1 mmol) was added over 2 minutes. The ice bath was removed, the flask was fitted with a reflux condenser and the reaction was heated to 40° C. Isoamyl nitrite (59.29 mL, 443.3 mmol) was added dropwise. The reaction was heated to reflux for 15 hours, cooled to ambient temperature, and concentrated. The resulting solids were suspended in 2 L water, stirred vigorously for 15 minutes, filtered, and washed with water (1 L). The resulting solid (75 g, still wet) was used directly in the next step.

Step E3: Preparation of 2-(1H-indazol-5-yloxy)-5-fluorobenzonitrile: 2-(1-Acetyl-1H-indazol-5-yloxy)-5-fluorobenzonitrile (369.4 mL, 221.7 mmol) in 370 mL MeOH was treated with 1.0 N HCl (243.8 mL, 243.8 mmol) at ambient temperature. The brown suspension was warmed to 70° C. for 28 hours and then cooled to 0° C. Sodium hydroxide (254.9 mL, 254.9 mmol) was added, followed by water (400 mL). The reaction was stirred at 0° C. for 15 minutes and then filtered. The solids were washed with water (1.5 and dried under high vacuum at 40° C. for 72 hours to provide 51.2 g of the desired product as a tan solid (91% yield for steps 2 and 3).

Step E4: Preparation of methyl 2-(5-(2-cyano-4-fluorophenoxy)-1H-indazol-1-yl)acetate: A flask was charged with 2-(1H-indazol-5-yloxy)-5-fluorobenzonitrile (125.7 g, 496.4 mmol), DMF (1250 mL), and $Cs_2CO_3$ (485.2 g, 1489 mmol). The flask was placed in a water bath (ambient temperature). Methyl 2-bromoacetate (103.4 mL, 1092 mmol) was added dropwise over a period of 20 minutes at ambient temperature. An additional 0.3 equivalents of methyl bromoacetate (14.10 mL, 148.9 mmol) were added and the mixture was stirred for additional 3 hours at ambient temperature. The mixture was filtered through a Celite pad and washed with DMF. The filtrate was concentrated under reduced pressure to provide 312 g of a dark tan solid. To the solid were added 1500 mL of EtOAc, 500 mL of water, and 300 mL of brine. The mixture was filtered through a GF paper to provide the desired product as a brown solid. The filtrate layers were separated and the aqueous layer was extracted with EtOAc. The filtered solid was added to the organic extracts. The combined extracts were washed with water and brine, dried over $MgSO_4$. The extracts were filtered through a Celite pad, concentrated under reduced pressure, and dried to provide 191.4 g of brown solid. The solid was transferred to a 4 L flask and dissolved in hot EtOAc (1250 mL). Hexane (1500 mL) was added with stirring, during which a light brown solid fell out of solution. The mixture was cooled to ambient temperature, and the solids were filtered, washed with 1:2/EtOAc: hexanes (750 mL), and dried under high vacuum to provide 128.6 g (79%) the desired product. $^1$H NMR (400 MHz, $CDCl_3$) δ 8.03, d, J=0.78 Hz, 1H), 7.41-7.36 (m, 3H), 7.22-7.16 (m, 2H), 6.81 (dd, J=4.29 Hz, 9.37 Hz, 1H), 5.19 (s, 2H), 3.79 (s, 3H).

Step E5: Preparation of 5-fluoro-2-(1-(2-hydroxyethyl)-1H-indazol-5-yloxy)benzonitrile: A flask was charged with methyl 2-(5-(2-cyano-4-fluorophenoxy)-1H-indazol-1-yl)acetate (100.0 g, 307.4 mmol) and MeOH (620 mL, 0.5M) and purged with nitrogen, Sodium borohydride (40.00 g, 1057 mmol) was added portionwise to the reaction mixture over 2.5 hours. The reaction mixture was cooled to ambient temperature and concentrated under reduced pressure. To the residue were added 1000 mL of saturated aqueous $NH_4Cl$ solution and 1000 mL of EtOAc. The mixture was stirred for 1 hour at ambient temperature. The layers were separated and the aqueous layer was extracted with EtOAc. The combined extracts were washed with saturated $NH_4Cl$ and brine, dried over $MgSO_4$, filtered through a Celite pad, and concentrated under reduced pressure to provide 91.1 g of the crude product. The crude solid was dissolved in $CH_2Cl_2$ (1500 mL). Hexanes (2500 mL) were added to the solution with stirring. The light brown solid which crashed out of solution was filtered, washed with 1:2 $CH_2Cl_2$:hexanes and dried under high vacuum to provide 84.8 g (92.8%) of the title product. $^1$H NMR (400 MHz, $CdCl_3$) δ 7.98 (s, 1H), 7.50 (d, J=8.98 Hz, 1H), 7.39-7.35 (m, 2H), 7.21-7.15 (m, 2H), 6.80 (dd, J=4.29 Hz. 9.37 Hz, 1H), 4.49 (t, J=5.00 Hz, 2H), 4.19-4.10 (m, 2H), 2.90 (br s, 1H).

Step E6: Preparation of 2-(5-(2-(aminomethyl)-4-fluorophenoxy)-1H-indazol-1-yl)ethanol dihydrochloride: A 2.5 L Parr reaction vessel was charged with 5-fluoro-2-(1-(2-hydroxyethyl)-1H-indazol-5-yloxy)benzonitrile (25.00 g, 84.09 mmol), EtOH (8.40 mL, 0.1M), and Pearlmans catalyst (5 g, 20% weight) and purged with nitrogen. Concentrated HCl (70.08 ml, 840.9 mmol) was added to the mixture. The vessel was charged with nitrogen gas (to 30 psi×3) and hydrogen (to 50 psi×3), and the reaction was stirred at ambient temperature for 66 hours. The mixture was filtered through a Celite pad and the pad was washed with EtOH. The filtrate was concentrated under reduced pressure, and the residue was azeotroped with EtOH and toluene to provide light brown solid to provide 30.2 g (96.0%) of the title compound. $^1$H NMR (400 MHz, $CD_3OD$) δ 8.07 (s, 1H), 7.72 (d, J=8.61 Hz, 1H), 7.42 (d, J=2.35 Hz, 1H), 7.33 (dd, J=3.13 Hz, 8.61 Hz, 1H), 7.29 (dd, J=2.35 Hz, 8.61 Hz, 1H), 7.12 (dt, J=3.13 Hz, 8.61 Hz, 1H), 6.83 (dd, J=4.70 Hz, 8.61 Hz, 1H), 4.54 (t, J=5.48 Hz, 2H), 4.25 (br s, 2H), 3.98 (t, J=5.48 Hz, 2H).

Step F: Preparation of 1-((5-fluoro-2-(1-(2-hydroxyethyl)-1H-indazol-5-yloxy)phenyl)methyl)-3-(3-(1-hydroxy-2-methylpropan-2-yl)-1-p-tolyl-1H-pyrazol-5-yl)urea: 2,2,2-Trichloroethyl 3-(1-hydroxy-2-methylpropan-2-yl)-1-p-tolyl-1H-pyrazol-5-ylcarbamate (0.010 g, 0.024 mmol) was added to a minimal amount of DMA, 2-(5-(2-(Aminomethyl)-4-fluorophenoxy)-1H-indazol-1-yl)ethanol (prepared in steps E1-E6; 0.0079 g, 0.026 mmol) and DEA (0.0084 mmol, 0.048 mmol) were added, and the reaction mixture was stirred at ambient temperature overnight. The reaction mixture was concentrated to remove the majority of DMA. The residue was purified by silica gel chromatography using 5% MeOH in ethyl acetate to provide 7 mg of the title compound. MS M+1 (573).

Example 2

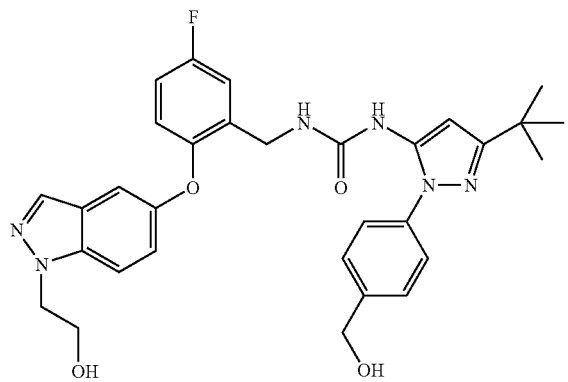

1-(3-tert-butyl-1-(4-(hydroxymethyl)phenyl)-1H-pyrazol-5-yl)-3-(5-fluoro-2-(1-(2-hydroxymethyl)-1H-indazol-5-yloxy)benzyl)urea Step A: 4-(5-Amino-3-tert-butyl-1H-pyrazol-1-yl)benzonitrile: A flask was charged with 4-hydrazinylbenzonitrile hydrochloride (0.70 g, 3.8 mmol.), 4,4-dimethyl-3-oxopentanenitrile (0.48 g, 3.8 mmol) and MeOH and the reaction was heated at refluxed overnight. The reaction was cooled, and the solids which formed upon cooling were filtered off and discarded. Additional solids formed upon further standing (product) along with product material in solution. The solution containing, the solids was concentrated to yield 0.75 g of solid product (92%). MS M+1 (241).

Step B: 2,2,2-Trichloroethyl 3-tert-butyl-1-(4-cyanophenyl)-1H-pyrazol-5-ylcarbamate: 4-(5-Amino-3-tert-butyl-1H-pyrazol-1-yl)benzonitrile (11.8 g, 49.1 mmol) was added to 70 mL of 3 N NaOH and 100 mL of ethyl acetate and the reaction mixture was cooled in an ice-bath. 2,2,2-Trichloroethyl carbonochloridate (9.34 mL, 68.7 mmol) was slowly added and the reaction was warmed to ambient temperature with stirring overnight. The ethyl acetate layer was washed with 3 N HCl and brine, and the organic layer was dried over $MgSO_4$, filtered and concentrated to an oil. Hexane was added to this oil and the mixture was stirred rapidly until a solid formed. The solids were triturated in hexanes, filtered, and dissolved in minimal warm ethyl acetate. Hexanes were added to the ethyl acetate solution until a slight cloudiness was observed. Material was allowed to crystallize and the solids were collected by filtration to yield 6.3 g of the desired product as a white solid, MS M+1 (416).

Step C: 1-(3-tert-butyl-1-(4-cyanophenyl)-1H-pyrazol-5-yl)-3-((5-fluoro-2-(1-(2-hydroxyethyl)-1H-indazol-5-yloxy) phenyl)methyl)urea: 2,2,2-Trichloroethyl 3-tert-butyl-1-p-tolyl-1H-pyrazol-5-ylcarbamate (0.22 g, 0.529 mmol), 2-(5-(2-(aminomethyl)-4-fluorophenoxy)-1H-indazol-1-yl) ethanol (prepared as in Example 1, Steps E1-E6; 0.175 g, 0.582 mmol), and triethylamine were combined in a minimal amount of DMA and stirred at ambient temperature overnight. The reaction mixture was concentrated, and the residue was diluted with DCM. The DCM was washed with aqueous $NH_4Cl$ and aqueous $Na_2CO_3$. The organic layer was dried over $MgSO_4$ and concentrated. The residue was purified by silica gel chromatography, eluting with 1% MeOH in ethyl acetate to provide 100 mg (32.6%) of the desired product. MS M+1 (568).

Step D: 1-(3-tert-butyl-1-(4-cyanophenyl)-1H-pyrazol-5-yl)-3-((5-fluoro-2-(1-(2-hydroxyethyl)-1H-indazol-5-yloxy) phenyl)methyl)urea hydrochloride: 1-(3-tert-Butyl-1-(4-cyanophenyl)-1H-pyrazol-5-yl)-3-((5-fluoro-2-(1-(2-hydroxyethyl)-1H-indazole-5-yloxy)phenyl)methyl)urea (0.070 g, 0.12 mmol) was added to MTBE and stirred. Saturated HCl in diethyl ether was added until a precipitate dropped out. The precipitate was collected by filtration and dried to provide 61 mg (83%) of the desired compound.

Step E: 1-(3-tert-butyl-1-(4-formylphenyl)-1H-pyrazol-5-yl)-3-((5-fluoro-2-(1-(2-hydroxyethyl)-(1H-indazol-5-yloxy)phenyl)methyl)urea: 1-(3-tert-butyl-1-(4-cyanophenyl)-1H-pyrazol-5-yl)-3-((5-fluoro-2-(1-(2-hydroxyethyl)-1H-indazol-5-yloxy)phenyl)methyl)urea hydrochloride (50 mg; 0.088 mmol) was added to 5 mL of DCM and the mixture was cooled in an ice bath. DIBAL (1.5 M; 0.05 g, 0.35 mmol) was added slowly. The reaction mixture was stirred for 1 hour. The reaction mixture was concentrated and quenched with 6 N HCl for 1 hour, then neutralized with $Na_2CO_3$. The reaction mixture was extracted with DCM and the organic layer was dried over $MgSO_4$. The organic layer was concentrated to provide 20 mg (22%; 55% pure) of the desired product. MS M+1 (571).

Step F: 1-(3-tert-Butyl-1-(4-(hydroxymethyl)phenyl)-1H-pyrazol-5-yl)-3-((5-fluoro-2-(1-(2-hydroxyethyl)-1H-indazol-5-yloxy)phenyl)methyl)urea: 1-(3-tert-butyl-1-(4-formylphenyl)-1H-pyrazol-5-yl)-3-((5-fluoro-2-(1-(2-hydroxyethyl)-1H-indazol-5-yloxy)phenyl)methyl)urea was treated with $NaBH_4$ in MeOH and stirred at ambient temperature for 2 hours. The reaction was quenched with 2 N HCl, then neutralized with $Na_2CO_3$ and extracted into DCM. The organic layer was dried and concentrated, and the residue purified on a pyridine column eluting with 20% ethanol in hexanes to provide 1.3 mg (6.3%) of the desired material. MS M+1 (573).

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A compound having the Formula I:

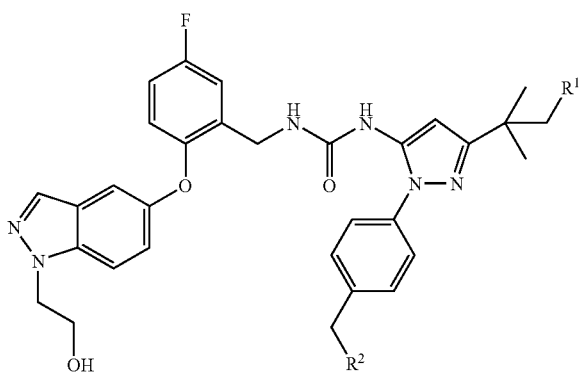

or a pharmaceutically acceptable salt thereof, wherein one of $R^1$ and $R^2$ is OH, the other being hydrogen.

2. A compound of claim 1, wherein $R^1$ is H and $R^2$ is OH.

3. A compound of claim 1, wherein $R^1$ is OH and $R^2$ is H.

4. A compound according to claim 1, which is in a pure and isolated form.

5. A pharmaceutical composition comprising a compound according to claim 1 and a pharmaceutically acceptable carrier.

6. A method of preparing a compound having the Formula I according to claim 1, comprising:

(a) coupling a corresponding compound of formula III

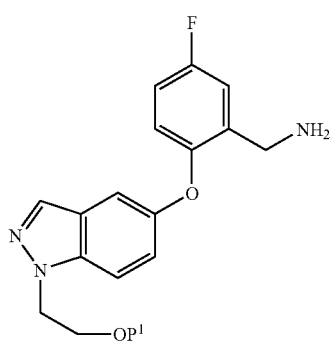

or a salt thereof, in which $P^1$ represents a hydrogen atom or a hydroxyl protecting group, with a corresponding compound of formula IV

IV

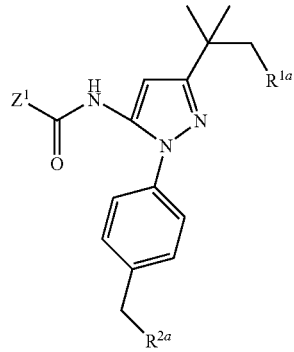

in which $Z^1$ represents a leaving group, or the corresponding isocyanate, and one of $R^{1a}$ and $R^{2a}$ is H and the other is $OP^2$ wherein $P^2$ is as defined for $P^1$; or (b) for a compound of Formula I wherein $R^1$ is H and $R^2$ is OH, treating a corresponding compound of formula V

V

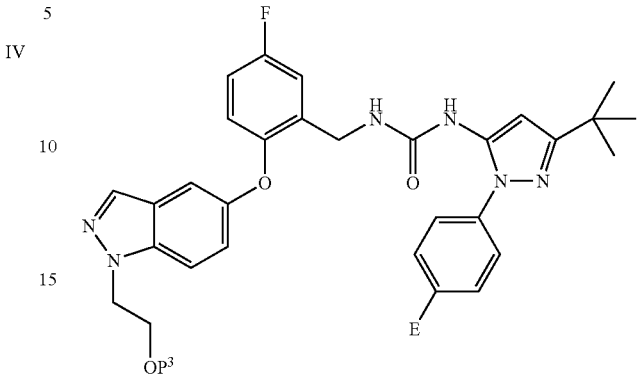

where $P^3$ is as defined for $P^1$ and E is CN, $CO_2$(1-3C alkyl) or C(=O)H, with one or more reducing agents capable of reducing the E group to a hydroxymethyl group followed by removing any protecting group and, if desired, forming a pharmaceutically acceptable salt.

* * * * *